US00PP08032P

United States Patent [19]

Cooper

[11] Patent Number: Plant 8,032

[45] Date of Patent: Nov. 17, 1992

[54] FUJI APPLE TREE: T.A.C. #114 STRAIN

[75] Inventor: Calvin L. Cooper, Brewster, Wash.

[73] Assignee: T.A.C. Co., Woodburn, Oreg.

[21] Appl. No.: 608,953

[22] Filed: Nov. 5, 1990

[51] Int. Cl.[5] ..... A01H 5/00
[52] U.S. Cl. ..... Plt./34.1
[58] Field of Search ..... Plt./34

[56] References Cited

U.S. PATENT DOCUMENTS

P.P. 7,001 8/1989 Hiraragi ..... Plt. 34

*Primary Examiner*—James R. Feyrer
*Attorney, Agent, or Firm*—Eugene D. Farley

[57] ABSTRACT

The T.A.C. #114 strain of Fuji apple trees characterized by the intense red coloration of its fruit, the high percentage of coloration of its fruit, the early maturity of its fruit, and the compactness of its tree.

2 Drawing Sheets

This invention relates to a new and distinct variety of apple tree, specifically to the Fuji apple tree variety denominated the T.A.C. #114 strain.

I discovered the new variety of apple tree in my cultivated apple orchard located at Brewster, Okanogan County, State of Washington in October of 1988.

At that time I noticed a single limb mutation developed on a 5 year old Redsport Type 2 Fuji apple tree (unpatented), also known as Red Fuji (Akifu #1), obtained from the B.C. Ministry of Agriculture, Summerland Station. The latter had as its parent a "Standard" strain of Fuji apple tree (unpatented), grown in Japan.

Two varieties of Fuji apple trees have been derived from the Akifu #1 strain. Although the nomenclature of these two selections is very confused, Redsport Type 1 has been accepted as the preferred name for the selections showing a striped color pattern and Redsport Type 2 the preferred name for the blush or solid color pattern. It has been determined by the U.S. Department of Agriculture that these two strains of Fuji are the only ones that have entered the U.S.A. legally.

As noted, Redsport Type 2 is the parent of my newly discovered Fuji apple variety.

At the time of discovery, I noticed that the single limb mutation on the five year old Redsport No. 2 of my new Fuji strain was characterized by a different growth pattern, exhibiting significantly more short spurs, shoots and dards on the two and three year old wood.

This growth pattern attracted my interest because it suggested the possibility of selecting a "spur type" Fuji apple tree that would be more productive and earlier fruiting than the standard Fuji apple tree, or other Fuji strains presently being planted or studied.

Accordingly, I asexually reproduced my new Fuji variety by grafting buds from the subject limb into growing trees on MM111 rootstock at Brewster, Wash.; on Mark rootstock at Woodburn, Oreg. and Pasco, Wash.; and on M26 trees at Orondo and Vantage, Wash.

Although it was the different growth pattern and compactness of growth that initially sparked by interest, I found when the first fruits developed in the Fall of 1989 that they were distinctly different from the fruits of all other known strains of Fuji.

First, they were a more brilliant tone of red color.

Second, the red color comprised of red on narrow red stripes, rather than a uniform coloration or blush.

Third, the red coloration covered from 80 to 95% of the total apple surface. This intense color makes the apple of my new variety much more attractive in appearance than are the fruits of the parent apple varieties, Fuji Redsport Type 2 and Fuji Standard.

Fourth, the amount of the fruit surface covered with red color significantly exceeds that of the parent strains of Fuji. On average, from 80 to 95% of the fruit surface is covered with red color in my new variety.

Fifth, the fruit of my new variety of Fuji apple tree are characterized by an advanced maturity. They develop a finished color and ripen from 10–14 days earlier than do the fruits of their predecessor Fuji strains.

In other characteristics, the fruits of my new apple variety are similar to those produced on the antecedent Fuji trees.

The above novel characteristics of my new apple variety Fuji T.A.C. #14 are summarized in the following Table:

| | FUJI T.A.C. #114 | FUJI Redsport Type 1 | FUJI Standard |
|---|---|---|---|
| Fruit finish color-shade | Red (5R 4/12) or Red (5R 5/13) (Nickerson) | Red (5R 4/12) or Red (5R 5/13) (Nickerson) | Red (5R 4/12) or Red (5R 5/13) (Nickerson) |
| Fruit finish color- % of surface | 80–95 | 50–65 | 25–40 |
| Early maturity of fruit- vs. Fuji Standard, in days | 10–14 | 00 | 00 |
| Branch internodal-distances (average in mm) | 16 | 22 | 22 |
| Average Shoot Length (m) | 1.1 | 1.3* | 1.3 |
| Spurs/Meter | 28.5 | 19.7 | 20.2 |

*Redspot Type 2

The foregoing characteristics are stable and have been observed to be constant for three generations.

The early maturity of the fruits of my newly discovered Fuji apple variety is of great economic importance, since it allows production of Fuji apples in areas where the growing season is too short for other Fuji strains to mature properly.

A more detailed botanical description of my new apple tree variety and of its fruit follows. The description is made with particular reference to the drawings, wherein.

BOTANICAL DESCRIPTION

Parentage: A single limb sport of a tree grafted to Redsport Type 2 Fuji.

Location of parent tree: Orchard of Calvin L. Cooper; Brewster, Wash., U.S.A.

Date of discovery: October 1988.

Date of fruit maturity: Oct. 18, 1989.

Tree: Medium vigorous, spreading, highly branched, productive.

Trunk: Stocky, smooth, gray green to light brown.

Branches: Spreading, wide angles, medium thick, lenticles medium, dispersed, white to light brown, branches profusely from leaf axillary buds.

Internodes: Average internode distance equals 16 mm vs 22 mm for Redsport #2, and Standard Fuji (trees growing on MM111 roots in same block).

Leaves (primary): Broad, dark green, glossy on upper surface moderately pubescent lower surface.

*Length.*—85 to 90 mm.

*Width.*—55 to 60 mm.

*Petiole.*—Short (15–18 mm) Thin (1.5–1.7 mm) pubescent.

*Margins.*—Serate.

*Tip.*—Sharply pointed.

*Bracts.*—Prominent, borne in pairs, opposite, narrow, pointed, born 3–4 mm from abscision zone.

Leaves (secondary): Oval, dark green upper surface, moderately pubescent lower surface.

*Length.*—55 to 60 mm.

*Width.*—40 to 45 mm.

*Margins.*—Slightly serate.

*Tip.*—Rounded.

*Petiole.*—Medium long (25–30 mm) Thin (1–1.5 mm).

*Bracts.*—Obscure, borne in pairs, opposite, hairlike, borne 1–2 mm from abscision zone.

Flowers: Mid Season (April 28–30 at Brewster, Wash.).

*Size.*—Medium.

*Color.*—White.

*Stamen.*—Single row, anthers flesh, yellow, turning dark brown with pollen shed.

*Pistil.*—Stigmas; broad, flat at top, rounded at base, styles; medium long, fused at base.

*Sepals.*—Medium size, pubescent.

*Pollination requirements.*—Satisfied by other diploid strains such as Golden Delicious, Winter Banana and commonly used strains of crab apples.

Figure 1:
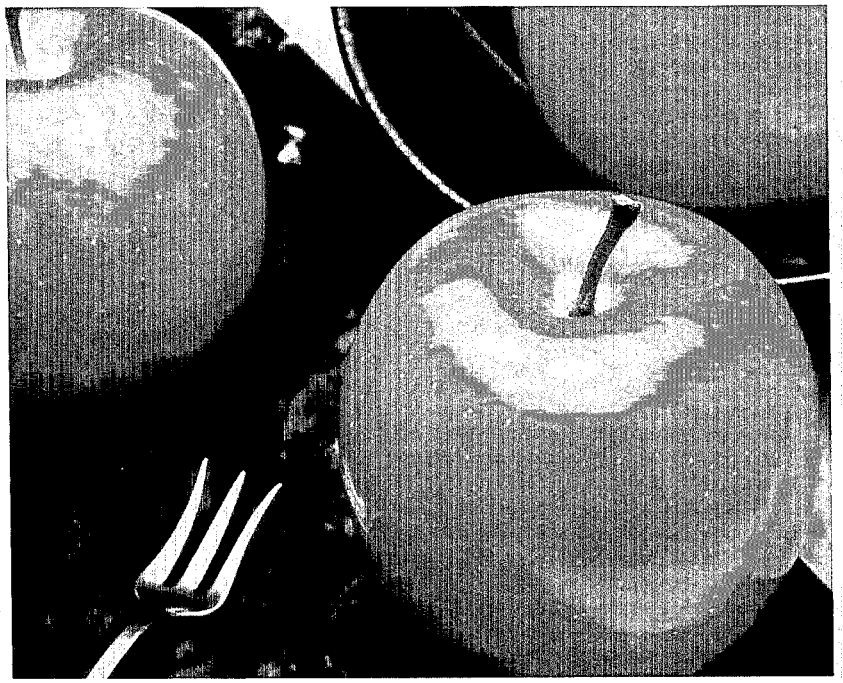
FIG. 1 is a view illustrating the intense red coloration of the mature fruits of my new apple variety, the red-on-red striping characteristic; and the high percentage of color over the entire fruit.

Fruit:

*Maturity when described.*—Eating ripe after 60 days cold storage. FIG. 1.

*Size.*—Medium (75 mm), to Large (100 mm).

*Form.*—Oval, slightly flattened at stem and calyx ends.

*Cavity.*—Round, narrow, deep: apex acuminate, breadth 25 mm, depth 15 mm.

*Stem.*—Medium short 18–20 mm, moderately thin 1.5 to 2 mm, moderately pubescent.

Figure 2:
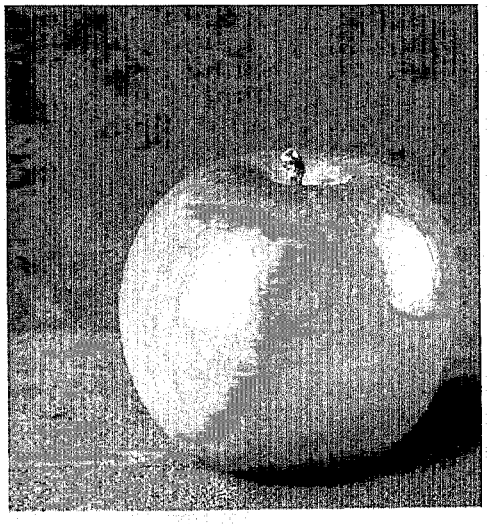
FIG. 2 is a view of the mature fruit of the immediate predecessor tree of my newly discovered variety, Redsport Type 2, also known as Red Fuji or Akifu #1, showing the color and striping pattern.
Figure 3:
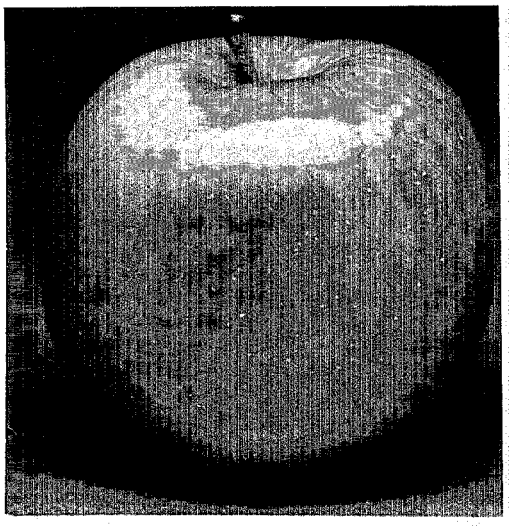
FIG. 3 is a view of the mature fruit produced by the grandparent of my new apple variety, the Standard strain of Fuji, showing the color and striping pattern.
Figure 4:
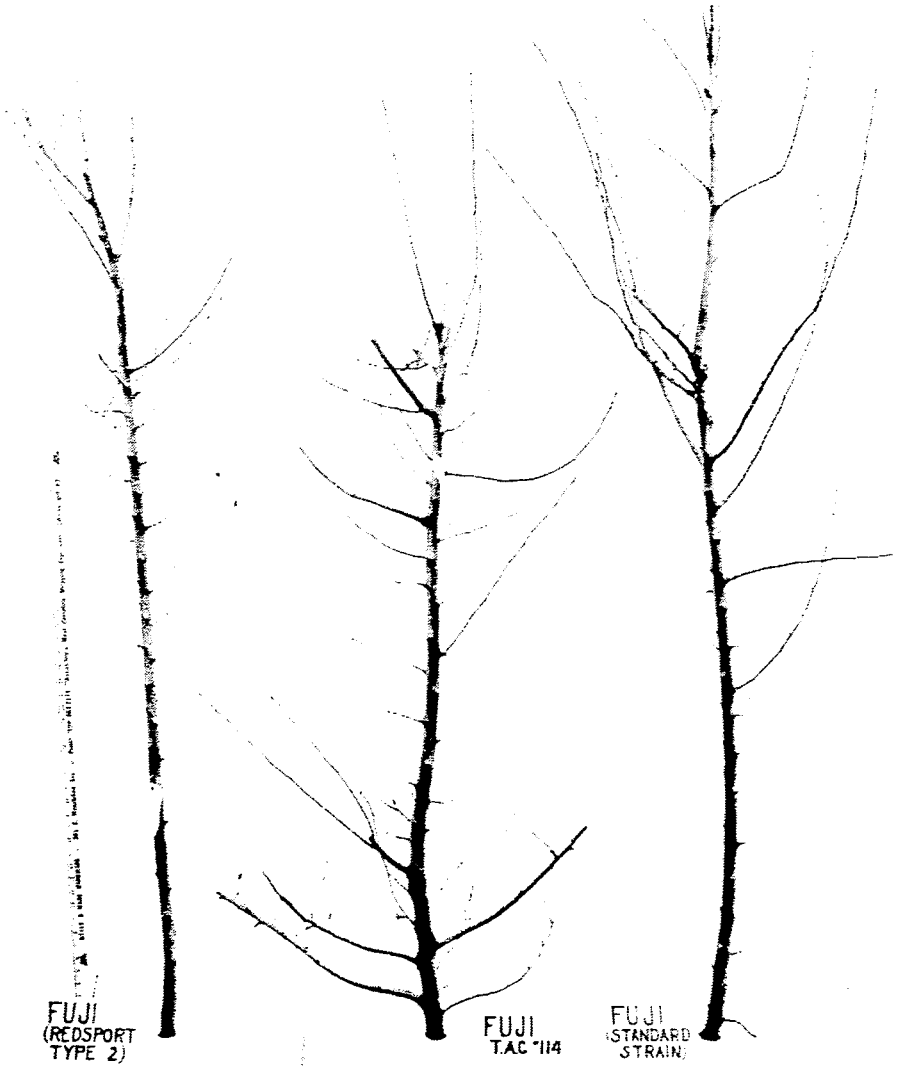
FIG. 4 is a composite view illustrating the branching habit of my new variety of apple tree Fuji T.A.C. #114 as compared with the branching habits of the established varieties Red Fuji (Redsport Type 2) and Fuji (Standard Strain).

*Skin.*—Smooth, glossy, red(5R 4/12)+ on red(5R 5/13)+ and yellow (Plate XVI, Color No. 21', Tone b)* striped. Red most prominent toward shoulder, thinning toward calyx, lenticles widely scattered, small. Red color covers 80 to 95 percent of the entire fruit surface (FIG. 1) compared to 25 to 40 percent for standard Fuji (FIG. 3) and 50 to 65 percent for Redsport Type 1 FIG. 2).

+Nickerson Color Fan — Munsell Color Company: see *System of Color Notation:* Munsell, A. H. (Brigham Young University Library QC 494.3 M85X)

**Ridgeway Color Standards & Nomenclature:* see *Color: Universal Language and Dictionary of Names:* Lowe, K. (Brigham Young University Library QC 494.3 K44X)

*Flesh.*—Creamy white turning very pale yellow with advanced maturity, juicy, sweet, smooth, tender, crisp, very fine.

*Aroma.*—Distinct, sprightly, moderately strong.

*Core.*—Sharply oval, bundle area medium, bundles — prominent.

*Basin.*—Smooth, shallow, rounded.

*Calyx.*—Lobes absent, sepals small, clasping, inconspicuous.

*Seeds.*—Medium size (6 to 7 mm long; 4 to 5 mm wide), brown, sharp at embryo end rounded distally.

Use: Fresh; dessert.

A comparison summary of the newly discovered Fuji Apple Tree T.A.C. #114 with the other established varieties of Fuji Apple tree, namely Fuji Standard, Fuji Redsport #2, and Yataka White (U.S. Plant Pat. No. 7,001) is as follows:

1. Standard Fuji has a significant degree of variation as to color pattern (some are striped and some blush). It apparently interacts with the growing conditions so that some years a given tree will produce both striped and/or blush fruit.

2. Fuji Redsport Type 2 is a selection of Fuji that was made at the Summerland B.C. Experiment Station. It was released to growers in British Columbia and from there was introduced into the United States. It was selected because it produced fruit that had more red color (typically 30 to 45% of the fruit surface is covered by red stripes) than does Fuji.

3. Fuji Yataka is a selection of Fuji that differs from its parent in that its fruit matures and colors about a month earlier than the fruit of Fuji Standard. The color pattern and the amount of surface colored by red color are not materially different from that characterizing the fruit of Standard Fuji.

4. Fuji T.A.C. #114 differs from the other strains in the following respects.

It exhibits a higher degree of red color development.

It is consistently striped in color pattern.

It has more spurs and dards and accordingly has less blind wood and a more compact growth habit.

It matures 10–14 days earlier than does Standard Fuji, but approximately 10 days later than Yataka Fuji.

All the other characteristics of Fuji T.A.C. #114 are the same as the characteristics of Standard Fuji. In particular the basin, calyx, lentical number and appearance, color tone, and skin are the same as Fuji Standard.

Flesh texture, sweetness, and flavor are the same as Fuji Standard.

Tree growth characteristics differ only in the more profuse spur development with leaf size, shape, margins petiole and color being indistinguishable from Fuji Standard. The flowers are also similar in every respect.

The fruits of Fuji T.A.C. #114 have the same storage and after-ripening characteristics as do the fruits of Fuji Standard, in terms of common and cold storage conditions.

I claim:

1. The new and distinct variety of Fuji apple tree substantially as herein shown and described, characterized particularly by the bright red color of its fruit, the red-on-red striped color pattern of its fruit, the high percentage of coloration of its fruit, and the compactness of the growth of the tree on which the fruit is borne.

* * * * *

Red Fuji (AKIFU 1)

Or Redsport Type 2
From B.C. on 4 year tree—Moderate vigor

Fuji (STANDARD STRAIN)

From Snake River, on 4 year tree
Moderate vigor